United States Patent [19]

Terada

[11] 4,310,228

[45] Jan. 12, 1982

[54] PHOTOGRAPHING APPARATUS FOR AN ENDOSCOPE

[75] Inventor: Masaaki Terada, Hachioji, Japan

[73] Assignee: Olympus Optical Co., Ltd., Tokyo, Japan

[21] Appl. No.: 105,785

[22] Filed: Dec. 20, 1979

[30] Foreign Application Priority Data

Jan. 11, 1979 [JP] Japan .................................. 54-1986

[51] Int. Cl.$^3$ ...................... G03B 15/03; G03B 29/00; A61B 1/04; A61B 1/06
[52] U.S. Cl. ........................................ 354/33; 354/34; 354/62; 128/6
[58] Field of Search ................... 354/27, 33, 34, 60 F, 354/62, 79, 131, 75, 76; 128/6-8; 350/19; 328/9

[56] References Cited

U.S. PATENT DOCUMENTS 3,307,107 2/1967 Kagan ................................. 354/131
4,153,356 5/1979 Hama .................................. 354/62

Primary Examiner—L. T. Hix
Assistant Examiner—William B. Perkey

[57] ABSTRACT

A photographing apparatus for an endoscope, which comprises an endoscope body (10) including an obervational optical system ($12_1$) and a fiber light guide (14), a light source unit (46) including a light source section (21) for providing light to the fiber light guide (14) and a camera (32) mounted on a light path, through which an optical image led out through the observational optical system ($12_1$) proceeds.

The camera (32) includes a photoelectric converter (34) disposed on the afore-mentioned light path of the optical image for producing a brightness signal (E10) corresponding to the brightness of said optical image and a transmitter (36) receiving the brightness signal (E10) from the photoelectric converter (34) and producing a transmission signal (E20) corresponding to the brightness signal (E10).

The light source unit (46) includes a receiver (42) receiving the transmission signal (E20) and producing a feedback signal (E30) corresponding to the brightness signal (E10) and a light source section control device (44) for controlling the light source section (21) according to the feedback signal (E30) for controlling the quantity of light provided from said light source section (21) to said fiber light guide (14).

In the photographing apparatus of the above construction, the camera (32) and light source device (46) are coupled together by transmission signal or electromagnetic wave (E20) without need of any electric contact.

5 Claims, 20 Drawing Figures

PHOTOGRAPHING APPARATUS FOR AN ENDOSCOPE

BACKGROUND OF THE INVENTION

This invention relates to a photographing apparatus for an endoscope, which is used for automatic exposure signal circuits, and in which the coupling between a camera and the endoscope and/or coupling between the endoscope and a light source unit are free from mechanical electric switches or contacts.

In the usual photographing apparatus for an endoscope, a camera and a light source for the endoscope are electrically coupled together. This coupling is made for the purposes of synchronizing flashlight for photographing and shutter release action and obtaining automatic exposure control. Usually, the coupling is accomplished through a plurality of mechanical electric switches or contacts provided in a connector section on the side of an eyepiece section of the endoscope. These switches or contacts are all exposed on the outer surface of the connector section, so that contact failure is likely to result from such causes as their contamination, oxidation and corrosion. This drawback can be avoided by adopting a water-proof construction for the switches. However, water-proof electric switches are complicated in construction and cannot fundamentally solve the problem.

There are teachings concerning the solution of the above problem, for instance one disclosed in Japanese Patent Disclosure No. 38322/78. In this disclosure, a light emission device is provided in the camera, and a light reception device is provided in the light source section. Light emitted from the light emission device is transmitted through a signal light guide within the endoscope to the light reception device. The disclosed apparatus makes use of light emitted from the light emission device as a synchronizing signal for the flashlight. Thus, no mechanical electric switches for the synchronization purposes are needed. However, this apparatus cannot be adopted where the automatic exposure control is made on the light source side.

SUMMARY OF THE INVENTION

The invention is contemplated in the light of the above circumstances, and its object is to provide a photographing apparatus for an endoscope, which enables the coupling of the camera and endoscope light source unit for the automatic exposure control without need of any mechanical electric switch.

According to the invention, the above object is achieved by a photographing apparatus for an endoscope, which comprises an endoscope body including an observational optical system and a light guide, a light source for providing light to the light guide, a photographing means mounted on a light path, through which an optical image obtained by light given to the light guide and led out through the observational optical system proceeds, a photoelectric converting means disposed on the light path of the optical image and serving to produce a brightness signal corresponding to the brightness of the optical image, a transmitting means connected to the photoelectric converting means and serving to produce a transmission signal corresponding to the brightness signal, a receiving means serving to produce a feedback signal corresponding to the brightness signal by receiving the transmission signal and a control means to control the light source according to the feedback signal for controlling the quantity of light provided from the light source to the light guide.

The photographing apparatus of the above construction has the following advantages:

In the first place, no electric switches or contacts exposed on the outer surface of the endoscope are needed, so that not only the water-proof construction of the endoscope is simplified but also freedom from the problem of contact failure due to contamination, oxidation or corrosion of electric switches or contacts can be obtained.

In the second place, since it is possible to select a frequency band used for transmission and/or reception, a plurality of photographing apparatus can be concurrently used without the possibility of malfunction due to radio interference. In addition, wrong use of the individual photographing apparatus can be avoided by providing each apparatus with an identification indication.

In the third place, there is no need of providing any electric wire for signal transmission or signal transmission light guide in the light guide protective tube connecting the endoscope and light source unit or like curved portions. Thus, no signal transmission wire breakage trouble results. In addition, since no signal transmission light guide is needed, satisfactory flexibility of the light guide protective tube can be ensured.

BRIEF DESCRIPTION OF THE DRAWINGS

FIGS. 3A and 3B to 5A and 5B are perspective views showing modifications of the examples of FIGS. 2A and 2B;

DESCRIPTION OF THE PREFERRED EMBODIMENT

An embodiment of the invention will now be described with reference to the accompanying drawings. In the drawings like parts are designated by like reference symbols for the sake of avoiding repeated explanation.

Figure 1:
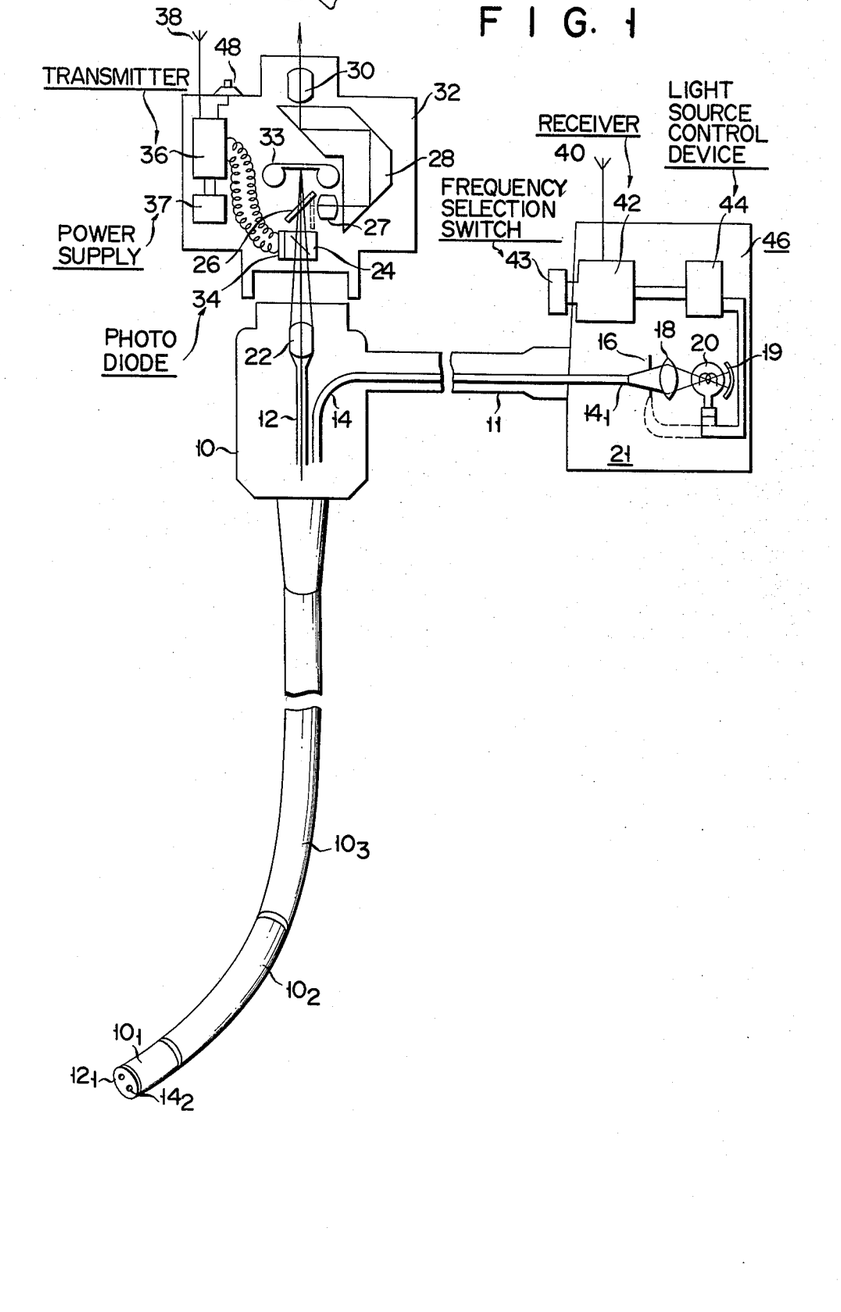
FIG. 1 is a schematic representation of an embodiment of the photographing apparatus for an endoscope according to the invention.

FIG. 1 is a schematic representation of an embodiment of the invention. An endoscope body 10 has a fiber image guide 12 for transferring an optical image and a fiber light guide 14. Light from a lamp 20 is coupled through a condenser lens 18 and a diaphragm 16 to a light receiving end $14_1$ of the fiber light guide 14. A reflector 19 is disposed on the back of the lamp 20 to increase the illumination efficiency. The diaphragm 16 and lamp 20 constitute a light source section 21. Light coupled to the light receiving end $14_1$ of the fiber light guide 14 is led therethrough and emitted from a light guide end $14_2$ of a distal end $10_1$. The distal end $10_1$ is connected through a bendable section $10_2$ and a flexible tube (insertion tube) $10_3$ to the endoscope body 10. The distal end $10_1$ has a conventional observational optical system $12_1$ provided within it. An optical image of a foreground subject caught by the optical system is led through the fiber image guide 12 to a lens system 22. The optical image having been transmitted through the lens system 22 is transmitted through a semi-transparent prism 24 and led to a movable mirror 26. When photographing is not made, the optical image incident on the movable mirror 26 is led through a lens system 27, a penta-prism 28 and a lens system 30 to the outside of the camera 32, which is mounted on the endoscope 10. When taking a picture, the movable mirror 26 is moved to a position of broken lines in FIG. 1. As a result, the optical image having been transmitted through the semi-transparent prism 24 is led to a film 33.

The afore-mentioned optical image is spectroscopically split by the semi-transparent prism 24, and part of it is led therefrom to the left in FIG. 1. The prism 24 is provided at its left hand end with a photoelectric converter or photo-diode 34. As the photoelectric converter may be used a cadmium sulfide (CdS) cell or a solar battery as well. The photo-diode 34 produces a brightness signal at a level corresponding to the brightness of the optical image transmitted through the prism 24. This brightness signal is coupled to a transmitter 36 of AM or FM type. The transmitter 36 produces a transmission signal corresponding to the afore-said brightness signal. The transmission signal is transmitted to the outside via an antenna 38. A power supply 37 is connected to the transmitter 36. The transmission signal radiated from the antenna 38 is intercepted by an antenna 40, and thence it is coupled to a receiver 42. Where the transmitter 36 is of FM type, the receiver is also of FM type. The receiver 42 demodulates a feedback signal corresponding to the transmission signal. The tuning frequency of the receiver 42 can be varied by a frequency selection switch 43, which serves to switch the resonance frequency of an LC tuning circuit in the receiver 42. Where the receiver 42 is provided with a so-called frequency synthesizer tuner, the dividing ratio of a programmable frequency divider within the synthesizer is varied by the switch 43.

The demodulated feedback signal is coupled from the receiver 42 to a light source control device 44. This control device 44 provides a control signal to the light source section 21 and may have a conventional construction. The quantity of light given from the light source section 21 to the light receiving end $14_1$ of the fiber light guide 14 can be controlled by controlling the power supplied to the lamp 20, the on-off frequency of the lamp 20 or the aperture of the diaphragm 16 according to the afore-mentioned control signal. The light source section 21, control device 44 and receiver 42 constitute a light source unit 46. The light source unit 46 is installed on the endoscope 10 via a light guide protective tube 11. In the construction of FIG. 1, an automatic control system having a closed loop including the foreground subject (not shown) such as the colon membrane present ahead of the distal end $10_1$. When the foreground subject is dark, the optical image led to the photo-diode 34 is also dark. In this case, the level of the brightness signal produced from the photo-diode 34 is low, so that modulation is obtained in the transmitter 36 to little extent. In consequence, the level of the demodulated feedback signal in the receiver 42 is low. When the level of the feedback signal is low, the light source control device 44 acts to increase the current supplied to the lamp 20 or on-off frequency of the lamp 20 or the aperture of the diaphragm 16. As a result, the quantity of light given to the fiber light guide 14 is increased to make the foreground subject brighter.

By the afore-mentioned automatic control action the brightness of the optical image led out from the fiber image guide 12 can be automatically controlled to a desired level.

The photographing apparatus shown in FIG. 1 is used in the following way. When taking a picture after mounting the camera 32 on the endoscope body 10, the eyepiece (not shown) of the endoscope is removed from the optical path. The movable mirror 26 is set at its position of solid lines in FIG. 1 until a spot to be photographed is found out. When the photographing spot is determined, a shutter release switch 48 is depressed. As a result, the transmitter 36 is rendered operative, and a synchronizing signal is transmitted therefrom. With the operation of the shutter release switch 48 the movable mirror 26 is moved to its position of broken lines in the Figure. When the synchronizing signal is captured by the receiver 42, the lamp 20 is caused to flash. The flashlight is reflected by the afore-mentioned photographing spot ahead of the distal end $10_1$, and the optical image of the spot is led through the semi-transparent prism 24 to the film 33. The brightness of the optical image at this time is detected by the photo-diode 34 and transmitted through the transmitter 36 and receiver 42 to the light source control device 44. When an adequate quantity of exposure light is obtained, the illumination by the lamp 20 is interrupted. During the "off" period of the lamp the movable mirror 26 is returned to the position of solid lines in the Figure, and then the illumination by the lamp 20 is resumed. In this way, one photographing cycle or sequence is ended. The adequate exposure light quantity is suitably determined in dependence upon the sensitivity of the film 33 used and other conditions.

The above description was concerned with the case of controlling the exposure on the side of the light source unit 46. However, it is also possible to adopt a system, in which the exposure control is made on the side of the camera 32 (i.e., a camera 32 of EE type is used) with only the synchronizing signal transmitted to the light source unit.

FIGS. 2A and 2B to 5A and 5B are perspective views showing examples of the camera 32 and light source unit 46 separated from the endoscope body 10. The camera 32 and the light source unit 46 are each given an identification indication 50, for instance using a numeral such as "3". Such an indication is given from the following ground. In frequent cases of endoscopic examination, several endoscopic sets are concurrently operated in the same place. In such a case, that is, when a plurality of the endoscopic photographing apparatus as shown in FIG. 1 are concurrently used, different frequencies are set for the individual photographing apparatus. This is done so because the use of a single frequency would lead to malfunction due to radio interference. Such malfunction can be avoided by providing exclusive frequency bands to the individual photographing apparatus such that do not overlap one another. However, when concurrently using a plurality of cameras 32 and associated light source units 46 for which different frequencies are set, it is likely that the user cannot tell which camera is paired with which light source unit. This inconvenience can be overcome by providing the afore-mentioned identification indication 50.

Figure 2A:
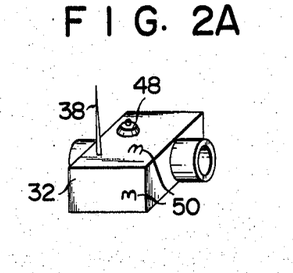
FIGS. 2A and 2B are perspective views showing examples of camera and light source unit provided with an identification indication.
Figure 2B:
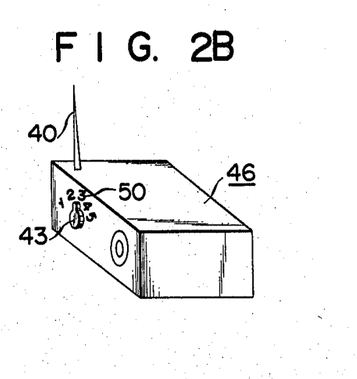
Figure 3A:
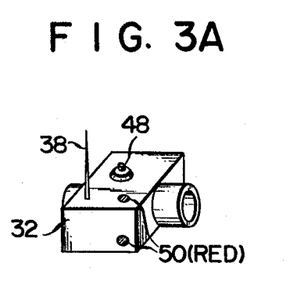
Figure 3B:
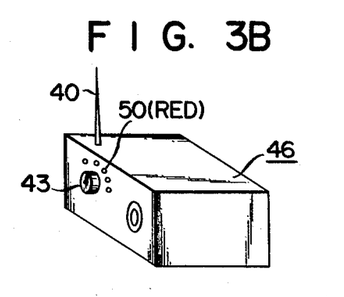
Figure 4A:
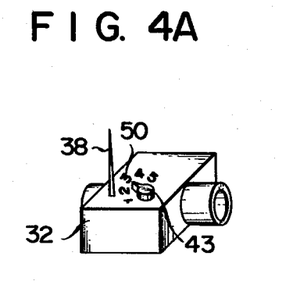
Figure 4B:
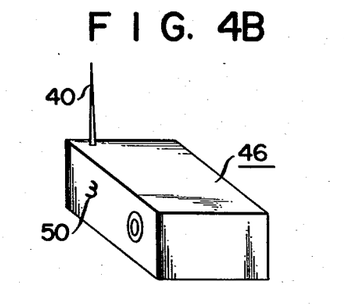
Figure 5A:
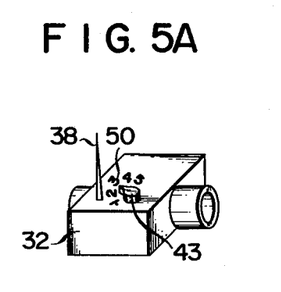
Figure 5B:
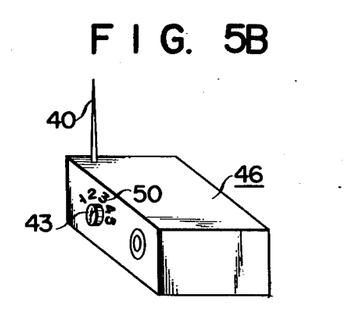

In the case of FIGS. 2A and 2B, the camera 32 is given an identification figure "3", and the frequency selection dial 43 of the light source unit 46 is set to a mark "3". In the case of FIGS. 3A and 3B, different colors are utilized for the identification indication. For instance, when the camera 32 has an identification color of, for instance, "read", the frequency selection dial 43 of the associated light source unit 46 is set to a red color mark. As the identification color may, for instance, be used black, blue, red, white and yellow. In the case of FIGS. 4A and 4B, a frequency selection dial 43 is provided on the side of the camera 32, and in the case of FIGS. 5A and 5B the frequency selection dial 43 is provided on both the camera 32 and light source unit 46.

Figure 6:
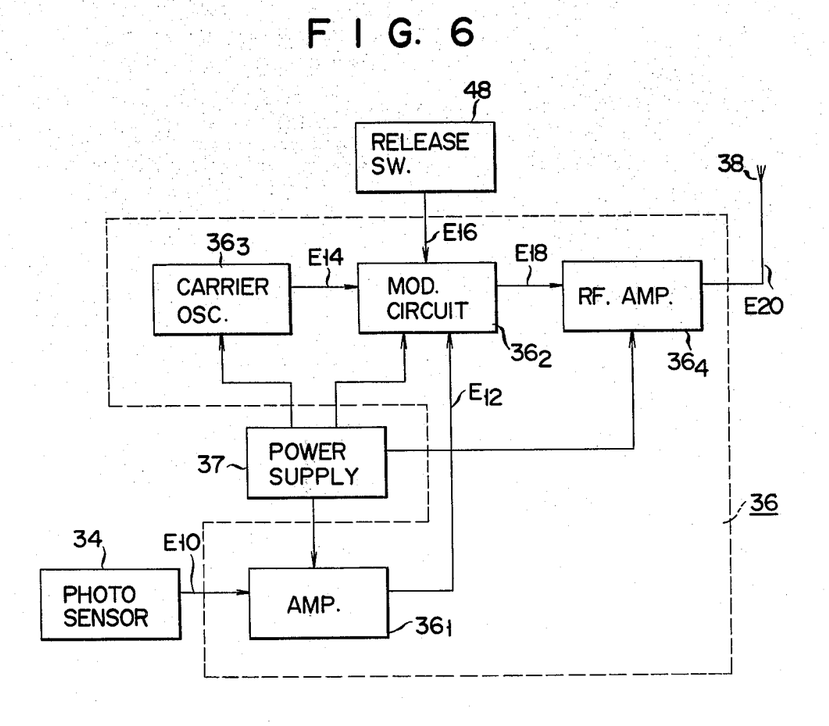
FIG. 6 is a block diagram showing an example of a transmitter 36 shown in FIG. 1.

FIG. 6 shows a specific construction of the transmitter 36 shown in FIG. 1. The photo-diode or photosensor 34 produces a brightness signal E10 which is coupled to an amplifier $36_1$ for amplification. The amplifier $36_1$ amplifies the signal E10 with a predetermined degree and produces a resultant modulation signal E12 which is coupled to a modulation circuit $36_2$. To the circuit $36_2$ is supplied a carrier wave signal E14 at a fixed frequency f1 from a carrier oscillator $36_3$. When the release switch 48 is depressed, an operation command signal E16 is provided from the switch 48 to the circuit $36_2$, whereupon the circuit $36_2$ produces a modulated carrier signal E18 produced by modulation of the carrier with the signal E12. The signal E18 is amplified by a radio-frequency amplifier $36_4$ to produce a transmission signal E20 which is supplied to the antenna 38. The components $36_1$ to $36_4$ are furnished with power from the power supply 37.

Figure 7:
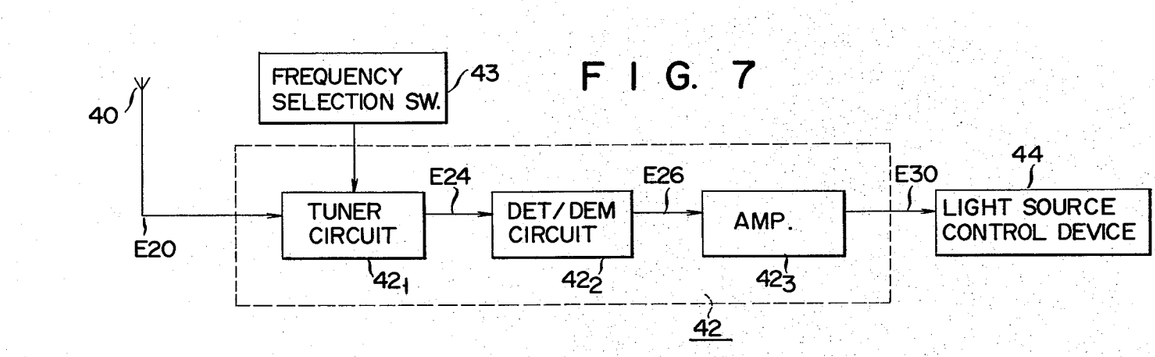
FIG. 7 is a block diagram showing an example of a receiver 42 shown in FIG. 1.

FIG. 7 shows a specific construction of the receiver 42. The transmission signal E20 intercepted by the antenna 40 is coupled to a tuner circuit $42_1$. The frequency selection switch 43 is set such that the tuning frequency f2 of the circuit $42_1$ is made equal to the carrier wave frequency or fixed frequency f1 of the camera 32 side. When the frequency selection switch 43 is set such that f1=f2, the circuit $42_1$ produces a first signal E24 corresponding to the signal E20. The signal E24 is coupled to a detector or demodulator circuit $42_2$. Where the modulation circuit $36_2$ shown in FIG. 6 is an AM modulator, the circuit $42_2$ is an AM detector, whereas when the circuit $36_2$ is an FM modulator the circuit $42_2$ is an FM demodulator.

The signal E24 is detected or demodulated by the circuit $42_2$ to produce a second signal E26 corresponding to the modulation signal component (E12) of the signal E20. The signal E26 is amplified by an amplifier $42_3$ to produce a feedback signal E30 corresponding to the signal E20. The signal E30 corresponds to the brightness signal E10 transmitted from the transmitter 36 to the receiver 42. In other words, the level of the signal E30 is changed with changes in the level of the signal E10.

Figures 8, 8A:
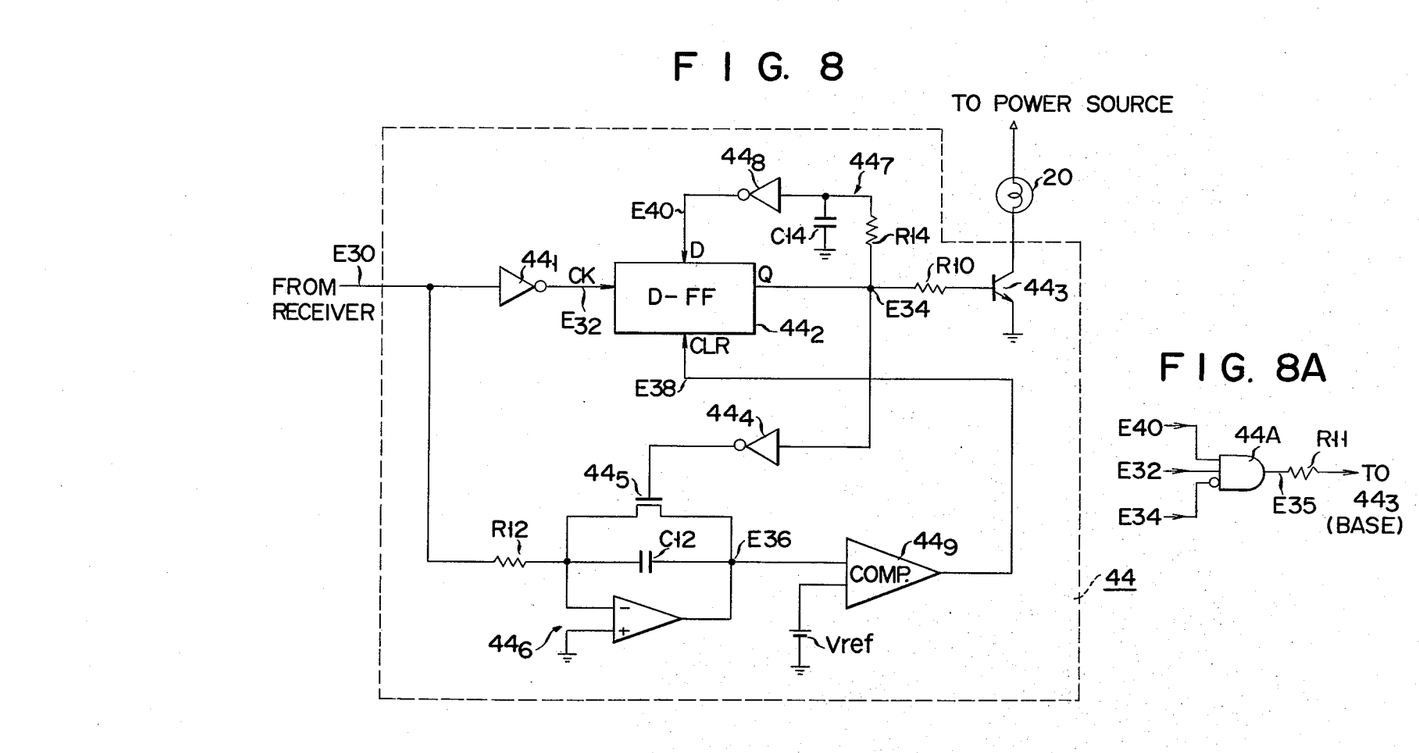
FIG. 8 is a block diagram showing a light source control device 44 shown in FIG. 1.
FIG. 8A shows an auxiliary circuit to be used with the circuit of FIG. 8.
Figure 9A:
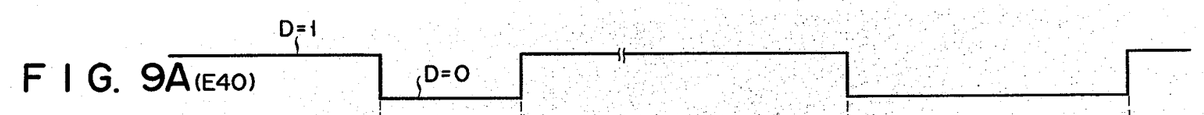
FIGS. 9A to 9F form a timing chart for illustrating the operation of the circuit shown in FIG. 8.
Figure 9B:
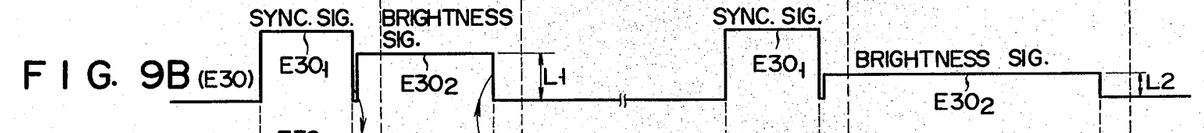
Figure 9C:
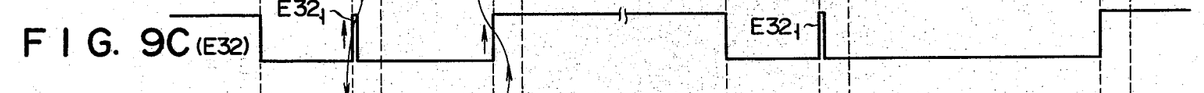

FIG. 8 shows a specific construction of the light source control device 44 shown in FIG. 1. FIGS. 9A to 9E represent a timing chart illustrating the operation of the device 44. The feedback signal E30 as shown in FIG. 9B is subjected to wave shaping and level inversion by an inverter $44_1$, whereby a signal E32 as shown in FIG. 9C is obtained. The signal E32 is coupled to a clock input terminal of a D type flip-flop (D-FF) $44_2$. Before an instant t14 a signal E40 of logic level "1" as shown in FIG. 9A is inputted at a D input terminal of the D-FF $44_2$. When the release switch 48 shown in FIG. 6 is turned on at an instant t10, the signal E30 is inverted to high level, while the signal E32 is inverted to low level. The D-FF $44_2$ is not clocked with the falling edge of the signal E32. Consequently, the output from the Q output terminal of the D-FF $44_2$ remains at logic level "0".

Figure 9D:
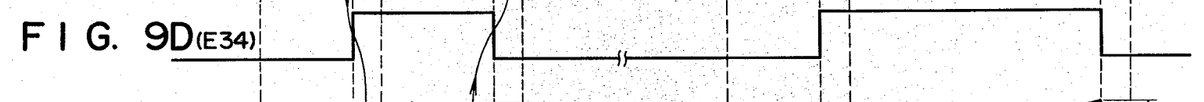

Until an instant t12 after the switch 48 has been turned on, the mirror 26 in the camera 32 is moved to the position of broken lines in FIG. 1. At the instant t12, the signal E30 is inverted again to low level, while the signal E32 is inverted again to high level. The signal E30 is used for its period of high level between the instants t10 and t12 as synchronizing signal $E30_1$. The pulse width of the signal $E30_1$ is determined by, for instance, a monostable multivibrator which is triggered with the rising edge of the signal E30, that is, the pulse width (between the instants t10 and t12) of the signal E30 can be determined according to the time constant of this multivibrator. The D-FF $44_2$ is clocked at the instant t12 with the rising edge of the signal E32. As a result, the signal E34 produced from the Q output terminal of the D-FF $44_2$ is inverted to logic level "1" as shown in FIG. 9D.

Figure 9E:
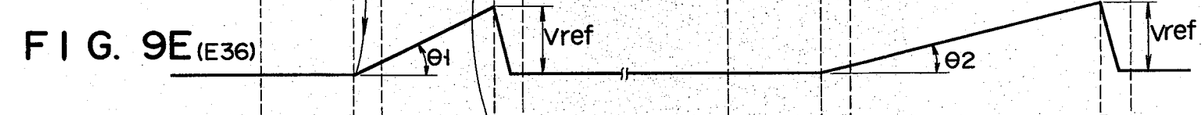

With the inversion of the signal E34 to logic level "1" at the instant t12, an NPN type drive transistor $44_3$ is biased through a resistor R10, whereupon the transistor $44_3$ is turned-on. As a result, the lamp 20 which is connected to the collector circuit of the transistor $44_3$ is energized to emit light. The logic "1" of the signal E34 is coupled after level inversion through an inverter $44_4$ to the gate of a MOS transistor $44_5$. When the gate potential on the transistor $44_5$ is reduced after the instant t12, the transistor $44_5$ is cut off. An integrating capacitor C12 of an integrator $44_6$ is connected between the drain and source of the transistor $44_5$. When the transistor $44_5$ is cut off, the integrator $44_6$ starts integration of the signal E30 which is supplied to an integrating resistor R12. The integration input to the integrator $44_6$ corresponds to the brightness of the optical image sensed by the photo-sensor 34 shown in FIG. 1 according to the glowing of the lamp 20 after the instant t12. In other words, after the instant t12 the signal E30 constitutes a brightness signal $E30_2$ having a level L1 corresponding to the brightness of the optical image as shown in FIG. 9B. This signal $E30_2$ is integrated by the integrator $44_6$ to produce an integration output signal E36 as shown in FIG. 9E.

The signal E34, which is level inverted at the instant t12, is coupled through a delay circuit $44_7$ consisting of a resistor R14 and a capacitor C14 to an inverter $44_8$. When the level of the input to the inverter $44_8$ exceeds a threshold level thereof, the inverter $44_8$ inverts the input level and produces the signal E40. In other words, the delay circuit $44_7$ delays the input signal after the instant t12, so that at an instant t14 the D input of the D-FF $44_2$ is inverted to logic level "0" as shown in FIG. 9A.

Figure 9F:
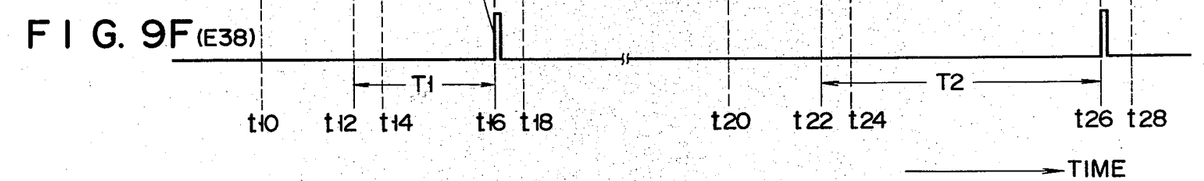

The integration output signal E36 from the integrator $44_6$ is coupled to a comparator $44_9$, which compares the signal E36 with a predetermined comparison voltage $V_{ref}$. Before an instant t16, $E36<V_{ref}$, so that the comparison output signal E38 from the comparator $44_9$ is at logic level "0". When $E36 \geq V_{ref}$ at the instant t16 is obtained as shown in FIG. 9E, the signal E38 is inverted to logic level "1" as shown in FIG. 9F. The signal E38 is coupled to a clear input terminal of the D-FF $44_2$. As a result, the D-FF $44_2$ is cleared at the instant t16, whereupon the signal E34 is inverted to logic level "0".

With the inversion of the signal E34 to logic level "0" at the instant t16, the transistor $44_3$ is cut off to turn off the lamp 20. As a result, light having previously been incident on the photo-sensor 34 in FIG. 1 or 6 disappears, so that the signal E10 is reduced substantially to zero level, reducing the modulation degree of the transmission signal E20 to zero. Then, the feedback signal E30 produced from the receiver 42 is reduced to zero level. When the signal E30 is reduced to zero level, the signal E32 is inverted to high level. The D-FF $44_2$ is clocked with the rising edge of the signal E32. However, since the D input has been at logic level "0" after the instant t14, the signal E34 is held at logic level "0" after the instant t16.

With the inversion of the signal E34 to logic level "0" at the instant t16, the transistor $44_5$ is turned-on to reset the integrator $44_6$. As a result, the signal E36 returns to zero level in a very short period of time as shown in FIG. 9E. When the condition $E36 < V_{ref}$ is satisfied again as a result of the resetting of the integrator $44_6$, the signal E38 is inverted again to logic level "0" immediately after the instant t16 as shown in FIG. 9F. The level inversion of the signal E34 at the instant t16 is transmitted through the delay circuit $44_7$ to the inverter $44_8$. When the level of the input to the inverter $44_8$ becomes lower than the threshold level at an instant t18, the signal E40 is inverted to logic level "1" as shown in FIG. 9A. After the instant t18 the same state as that before the instant t10 is maintained until the next synchronizing signal $E30_1$ of the signal E30 appears. After the instant t18 the release switch 48 shown in FIG. 6 is turned off, and as a result the mirror 26 shown in FIG. 1 is returned to its initial position.

If it is desired to cause glowing of the lamp 20 before the instant t10 and after instant t18 in FIGS. 9A to 9F, that is, when the mirror 26 shown in FIG. 1 is in the position of solid lines, a logic circuit as shown in FIG. 8A may be used. Here, the signals E40, E32 and E34 are coupled to an AND gate 44A, with the signal E34 being coupled to a level inversion input terminal. The AND output E35 of the gate 44A is coupled through a resistor R11 to the base of the transistor $44_3$. The output E35 is at logic level "1" before the instant t10 and after the instant t18, that is, during the periods when the shutter release switch 48 is not operated. During these periods, the transistor $44_3$ is thus "on", and the lamp 20 emits light.

With the control device 44 shown in FIG. 8, the lamp 20 emits light during the period of the "on" state of the transistor $44_3$, i.e., during the period between the instants t12 and t16, during which the signal E34 is at logic level "1". This period between the instants t12 and t16 corresponds to an exposure period T1 from the start of integration by the integrator $44_6$ (E36=0) until the signal E36 becomes equal to $V_{ref}$. This exposure period T1 is inversely proportional to the slope $\theta 1$ of the signal E36, and the slope $\theta 1$ is proportional to the level L1 of the brightness signal $E30_2$. This means that the exposure period T1 is inversely proportional to the brightness of the optical image sensed by the photo-sensor 34. In other words, the brighter the optical image the shorter the exposure period is, and the darker the optical image the longer the exposure period is.

The sequence of events that take place in case when the optical image is darker (i.e., L1>L2) are shown between instants t20 and t28 in FIGS. 9A to 9F. In this case, the slope of the signal E36 is reduced ($\theta 1 > \theta 2$), and the exposure period is increased (T1<T2). This means that the quantity of light given to the film 33 shown in FIG. 1 is automatically controlled to a predetermined value according to the brightness of the optical image. In this way, automatic exposure control can be obtained.

Figure 10:
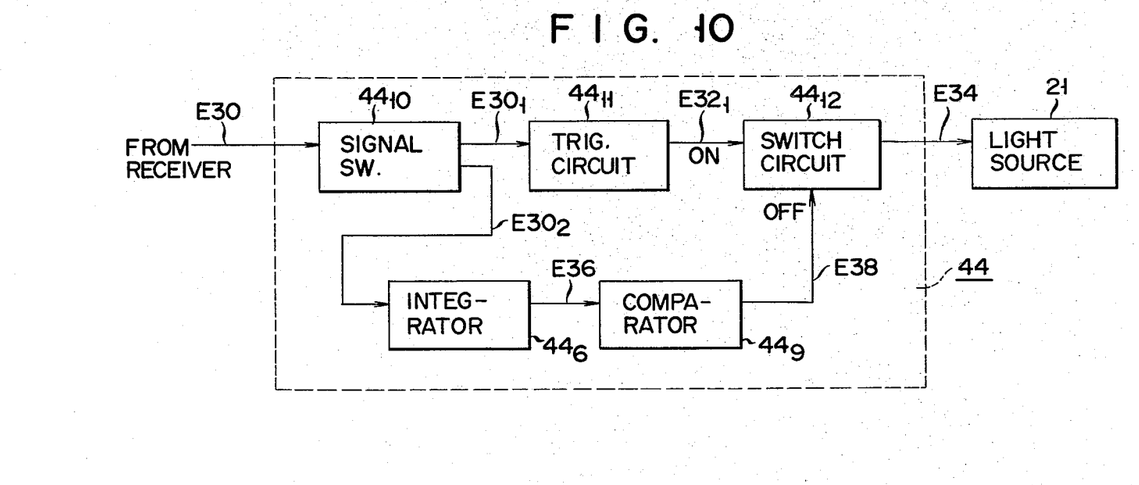
FIG. 10 is a block diagram showing a modification of the device 44 shown in FIG. 8.

FIG. 10 shows a modification of the control device 44 shown in FIG. 8. Here, the feedback signal E30 is coupled to a signal switch $44_{10}$, which is an analog gate circuit for separating the synchronizing signal $E30_1$ and brightness signal $E30_2$ in the signal E30. In other words, a portion of the signal E30 from the rising edge till the falling edge (i.e., between the instants t10 and t12 in FIG. 9B) is supplied as the signal $E30_1$ to a trigger circuit $44_{11}$. In consequence, the circuit $44_{11}$ produces a trigger pulse $E32_1$ with the falling edge of the signal $E30_1$ (at the instant t12 in FIG. 9C). The pulse $E32_1$ is inputted to a switch circuit $44_2$ which is constructed with an SCR or the like. When the pulse $E32_1$ is inputted, the circuit $44_{12}$ is turned on to supply the signal E34 (between the instants t12 and t16 in FIG. 9D) for causing the glowing of the lamp 20.

Meanwhile, a portion of the signal E30 from the second rising edge till the second falling edge (i.e., between the instants t12 and t16 in FIG. 9B) is inputted as the signal $E30_2$ to an integrator $44_6$. The integrator $44_6$ integrates the level L1 of the signal $E30_2$, and supplies the integration output signal E36 to a comparator $44_9$. The comparator $44_9$ is provided with a predetermined reference voltage $V_{ref}$, and couples a comparison output signal E38 to the circuit $44_{12}$ when a condition $E36 \geq V_{ref}$ is satisfied (at the instant t16 in FIG. 9F). When the signal E38 is inputted, the circuit $44_{12}$ is turned off, and the light source 21 stops light emission.

Although specific constructions have been illustrated and described herein, it is not intended that the invention be limited to the elements and constructions disclosed. One skilled in the art will recognize that the particular elements or sub-constructions may be used without departing from the scope and spirit of the invention.

What is claimed is:

1. A photographing apparatus for an endoscope comprising:
    an endoscope body including an observational optical system and a light guide;
    a light source for providing light to said light guide;
    a photographing means mounted on a light path, through which an optical image obtained by light given to said light guide and led out through said observational optical system proceeds;
    a photoelectric converting means disposed on said light path of said optical image for producing a brightness signal corresponding to the brightness of said optical image;
    a transmitting means connected to said photoelectric converting means for producing a transmission signal corresponding to said brightness signal;
    a receiving means connected by wireless means to said transmitting means for receiving said transmission signal and for producing a feedback signal corresponding to said brightness signal; and
    a control means for controlling said light source according to said feedback signal for controlling the quantity of light provided from said light source to said light guide.

2. A photographing apparatus according to claim 1, wherein at least either said transmitting means or said receiving means is provided with a frequency selection switch so that one of a plurality of transmitting and receiving frequencies may be selected for preventing radio interference with other photographing apparatus.

3. A photographing apparatus according to claim 1 or 2, wherein at least either said transmitting means or said receiving means is provided with a predetermined indication means showing that said transmitter and said receiver are combined and used together.

4. A photographing apparatus according to claim 1 or 2, wherein said feedback signal includes a synchronizing signal preceding said brightness signal and representing the timing of the shutter release action of said photographing means, and also wherein said control means includes a means for causing the control of said light source to be started in accordance with said synchronizing signal.

5. A photographing apparatus according to claim 3, wherein said feedback signal includes a synchronizing signal preceding said brightness signal and representing the timing of the shutter release action of said photographing means, and also wherein said control means includes a means for causing the control of said light source to be started in accordance with said synchronizing signal.

* * * * *